United States Patent [19]
Schwartz et al.

[11] Patent Number: 5,735,899
[45] Date of Patent: Apr. 7, 1998

[54] LOW PROFILE INTRAOSSEOUS ANTERIOR SPINAL FUSION SYSTEM AND METHOD

[75] Inventors: Herbert S. Schwartz; David K. Deboer; John M. Dawson, all of Nashville, Tenn.

[73] Assignee: Vanderbilt University, Nashville, Tenn.

[21] Appl. No.: 687,291

[22] Filed: Jul. 25, 1996

Related U.S. Application Data

[63] Continuation of Ser. No. 351,837, Dec. 8, 1994, abandoned.

[51] Int. Cl.⁶ .................................................. A61F 2/44
[52] U.S. Cl. ..................................... 623/17; 606/61
[58] Field of Search ......................... 623/17; 606/60, 606/61, 71

[56] References Cited

U.S. PATENT DOCUMENTS

| | | | |
|---|---|---|---|
| 4,401,112 | 8/1983 | Rezaian | 128/92 |
| 4,516,569 | 5/1985 | Evans et al. | 128/92 |
| 4,553,273 | 11/1985 | Wu | 623/18 |
| 4,636,217 | 1/1987 | Ogilvie et al. | 623/17 |
| 4,846,162 | 7/1989 | Moehring | 128/92 |
| 4,944,743 | 7/1990 | Gotzen et al. | 606/61 |
| 4,946,458 | 8/1990 | Harms et al. | 606/61 |
| 5,053,034 | 10/1991 | Olerud | 606/61 |
| 5,108,395 | 4/1992 | Laurain | 606/61 |
| 5,382,248 | 1/1995 | Jacobson et al. | 606/60 |

*Primary Examiner*—Michael J. Milano
*Attorney, Agent, or Firm*—Waddey & Patterson; Mark J. Patterson

[57] ABSTRACT

Disclosed herein is a system and implant designed for use in short segment anterior fusion of a patient's spine after the removal of a diseased or injured anterior vertebral body. The system includes the placement of the cylinder of the implant in an intraosseous location for added safety, and for the placement of the cylinder of the implant in the middle column area of the adjacent healthy vertebral bodies for increased biomechanical strength. The system further includes transverse fixation of the cylinder of the implant, thus adding medial-lateral and rotational support to the system. Finally, the system utilizes the concept of modularity, wherein intraoperative exchangeable parts are available to better fit the patient.

15 Claims, 9 Drawing Sheets

| CONSTRUCT | LOAD | AXIAL COMPRESSION MEAN STIFFNESS | 95% CI | TORSION MEAN STIFFNESS | 95% CI |
|---|---|---|---|---|---|
| I | 1 | 2.61 | 2.34, 2.86 | 7.9 | 5.6, 10.2 |
|   | 2 | 2.96 | 2.68, 3.24 | 8.0 | 6.0, 10.0 |
|   | 3 | 3.11 | 2.85, 3.36 | 7.5 | 6.0, 9.0 |
| S | 1 | 3.22 | 2.48, 3.98 | 6.0 | 5.4, 6.5 |
|   | 2 | 3.49 | 2.90, 4.07 | 5.6 | 5.0, 6.1 |
|   | 3 | 4.17 | 3.58, 4.77 | 4.9 | 4.4, 5.4 |
| SA | 1 | 2.94 | 2.05, 3.83 |   |   |
|   | 2 | 3.58 | 2.90, 4.25 |   |   |
|   | 3 | 4.25 | 3.45, 5.04 |   |   |
| P | 1 | 0.60 | 0.54, 0.66 | 5.0 | 4.4, 5.6 |
|   | 2 | 0.67 | 0.61, 0.73 | 4.9 | 4.5, 5.3 |
|   | 3 | 0.72 | 0.66, 0.78 | 4.8 | 4.4, 5.2 |
| PA | 1 | 2.76 | 2.43, 3.09 | 5.4 | 4.6, 6.2 |
|   | 2 | 2.96 | 2.66, 3.26 | 5.4 | 4.8, 6.0 |
|   | 3 | 3.09 | 2.81, 3.37 | 5.2 | 4.6, 5.8 |
| AA | 1 | 3.01 | 2.53, 3.50 | 6.1 | 4.3, 8.0 |
|   | 2 | 3.34 | 2.81, 3.88 | 5.4 | 4.6, 6.1 |
|   | 3 | 3.47 | 2.92, 4.01 | 5.1 | 4.5, 5.7 |

LOW PROFILE INTRAOSSEOUS ANTERIOR SPINAL FUSION SYSTEM AND METHOD

This application is a continuation of application Ser. No. 08/351,837, filed Dec. 8, 1994, now abandoned.

BACKGROUND OF THE INVENTION

The present invention relates generally to a system and method for the repair and fusion of a segment of the anterior spine following removal of part or all of vertebral body due to trauma or tumor. More particularly, the invention discloses a system for fusion of the anterior spine that employs the intraosseous insertion of a short segment, low profile implant or spinal nail within the middle column area of the anterior section of the spine, accompanied by transverse fixation of this implant. The anterior spine has separate requirements for reconstructive implants because it is distinctly different from the posterior spine in terms of anatomy, biomechanics and neoplastic/traumatic pathology.

It will be appreciated by those skilled in the art that the highly vascular vertebral bodies located anteriorly in the spinal column are a common site for bone metastases of a carcinoma. Primary malignant neoplasms of bone, sarcomas, also arise in the vertebral bodies. The anterior spine is frequently fractured and rendered unstable by high energy trauma. The fracture fragments will often compress the spinal cord or nerve roots and require removal of part of the vertebral body for purposes of decompression. This will further render the spine unstable. Unfortunately, it is difficult to safely and securely reconstruct or stabilize the spine after removal of an anterior vertebral body due to disease or trauma. A fusion system which includes a permanently implantable device preferably will have a low profile so that it will not protrude into the abdominal or thoracic cavity, as such critical neurovascular structures as the aorta and the inferior vena cava are located in close proximity to the anterior spine. This risk is particularly acute if a component of the implant should come free and migrate.

Furthermore, it is difficult to construct a fusion system that provides adequate axial, medial-lateral, and rotational stability. Such stability is necessary to keep the nerves which are to be protected in the spinal column from being compromised by excessive movement of the surrounding spinal structures. To this end, there have been several attempts to develop implantable anterior spinal support systems that provide for safety and for stability.

One such attempt is described in U.S. Pat. No. 4,553,273 issued to K. Wu on Nov. 19, 1985. The Wu '273 patent discloses a spinal implant which stabilizes the spinal column in a patient from whom vertebral bodies have been removed. The Wu implant is intended to be located in the intraosseous area of the anterior spine and designed to span the space created by a removed vertebral body. It is implanted in the healthy vertebral bodies adjacent to the empty space. The length of the implant can be adjusted by a set screw lying essentially at the mid-point of the implant. The Wu implant provides axial support. However, because it is attached solely by placement of the ends of the device into a slot in the adjacent vertebral bodies, it is deficient in medial-lateral and rotational support. Thus, the Wu '273 patent does not fully address the needs for safety and stability in the repair of the spinal structure which has been compromised by disease or trauma and has not gained the support of spinal surgeons.

Another implantable device is disclosed in U.S. Pat. No. 4,636,217 issued to I. W. Ogilvie and F. R. Ogilvie on Jan. 13, 1987. The Ogilvie '217 patent describes a spinal construct for implantation into a void created in the spinal column when a diseased or injured vertebrae has been removed. The implant is placed into the anterior spine and is fixed in place with bone screws extending vertically from the ends of the implant. The screws are driven into the adjacent upper and lower vertebrae after the insert has been positioned in place using a drive mechanism. The drive mechanism is accessible after the implant has been inserted. This drive mechanism has drive gears with a drive connection. The drive gears are operated by attaching a drive wrench to the drive connection and turning the drive wrench. The drive gears then rotate the self-tapping, bone-penetrating retaining screws, driving them into the adjacent vertebrae. The insert lies in an intraosseous position, with no parts extending outside the margin of the anterior vertebral column. The implant offers axial support, but because of the location of the attachment screws, the implant offers inadequate medial-lateral and rotational support.

Another attempt to create a spinal fusion system is found in U.S. Pat. No. 5,108,395 issued to J. Laurain on Apr. 28, 1992. The Laurain '395 patent discloses an implant for anterior spinal fusion. This implant lies on the surface of the anterior spine. Thus, it is an extraosseous device. As a result, the device is in closer proximity to vital internal structures and organs. Therefore, this orientation is less safe than an intraosseous orientation. Biomechanically, it cannot offer the strength of an intraosseous implant positioned within the middle column of the spine.

What is needed, then, is a system for anterior spinal fusion that uses a low profile intraosseous positioning device and that provides support for the anterior spine in the axial, medial-lateral, and rotational directions. Such a device is presently lacking in the prior art.

SUMMARY OF THE INVENTION

It is an object of this invention to provide a system designed to rigidly and safely achieve short segment anterior fusion of the spine.

It is a further object of this invention to provide a spinal fusion system that incorporates middle column reconstruction, thereby providing biomechanical strength and reproduction of the anatomic spinal sagittal curvature that other implants cannot duplicate.

Yet another object of this invention is to provide a spinal fusion system where the implant of the system is incorporated in an intraosseous location.

Another object of this invention is to provide a spinal fusion system wherein the implant device of the system is further secured by transverse locking bolts.

It is another object of this invention to provide a modular spinal fusion system with easy access to intraoperative exchangeable parts to better fit the patient and to facilitate adjustment or modification of the system after implantation.

Accordingly, the system of the invention includes a short segment low profile anterior spinal intraosseous implant. The cylindrical implant will preferably come in a variety of lengths and curvatures from which the surgeon can select one that provides the best fit. At each end of the implant are transversely oriented apertures adapted to receive locking bolts which pass through the implant and into healthy bone tissue on the opposite side, fixing it in place. Retainer plates are attached by screws across the surface of the bony tissues below the implant, to diffuse the compression forces of the locking bolts.

The implant of the system is surgically located in an intraosseous and middle column position to provide safety and biomechanical strength. The transverse fixation means are positioned laterally to further increase the safety of the system and provide the torsional rigidity of the invention.

After installing the system, the implant of the system and the void space created by the removal of a diseased or an injured vertebrae is filled in with bone graft. This grafting will increase the life of the system.

DESCRIPTION OF THE PREFERRED EMBODIMENT

The spinal fusion system of this invention can be applied to any injured region of the spine. Its safety features, as described more fully below, are particularly effective in the lumbar region of the anterior spine. The lumbar region of the anterior spine is just posterior to such vital structures as the aorta and the inferior vena cava, so safety is critical in this area.

Figure 1:
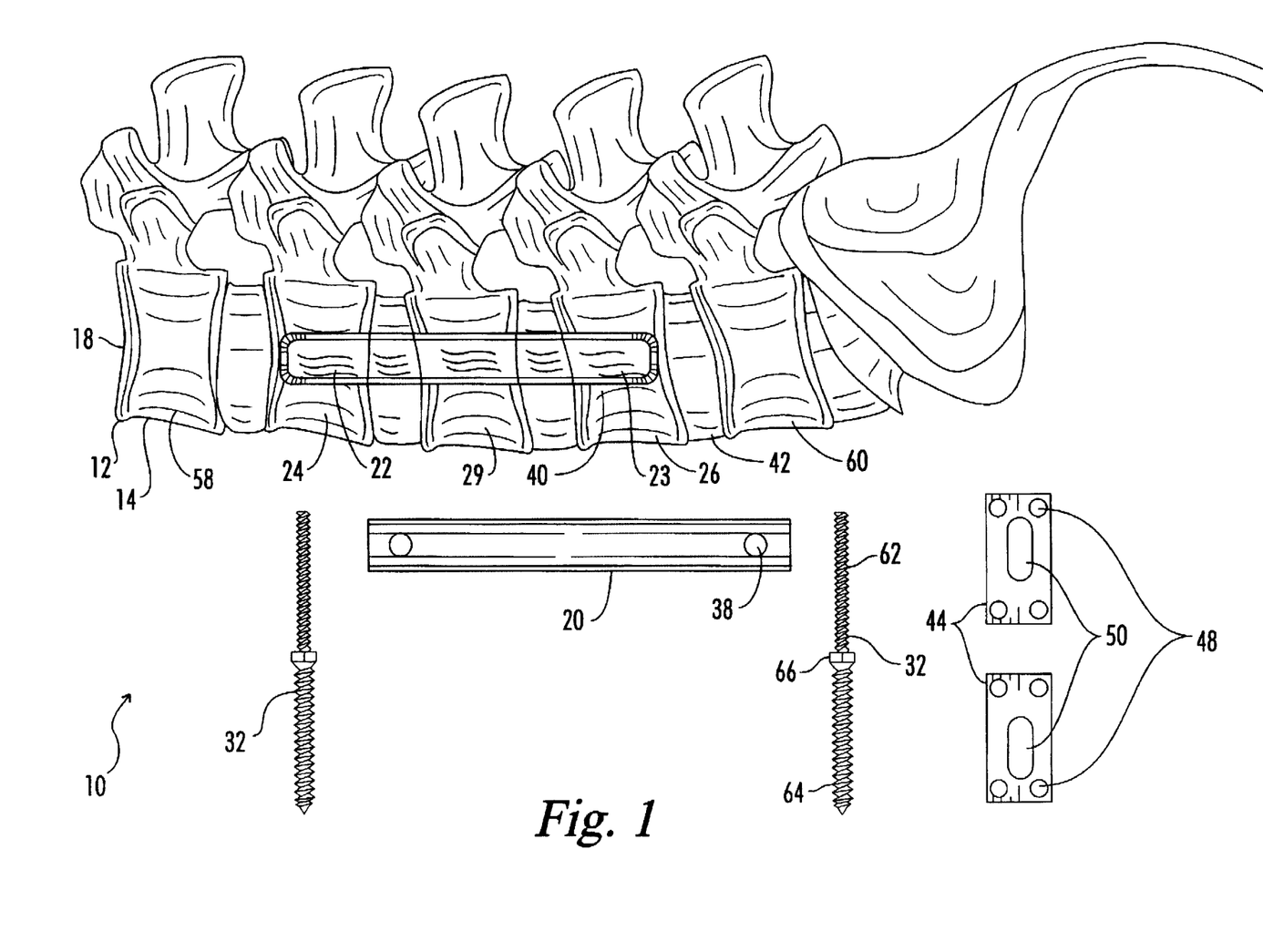
FIG. 1 is a plan view of the lumbar region of a porcine spine adjacent to the exploded components of the system of the present invention.

Referring now to the drawings wherein like numerals represent like parts throughout, a preferred embodiment of the system of the present invention is generally represented by the numeral 10. As best seen in FIG. 1, the system 10 includes an implant cylinder 20 and transverse fixation means, which in the preferred embodiment are transverse locking bolts 32. Preferably, the system 10 also includes retainer plates 44 to assist in secure placement of locking bolts 32.

As best seen on FIGS. 1, 2, 7, 9A, and 9B, implant 20 is preferably a hollow cylinder made of a biocompatible metal. The length of implant 20 will vary depending on the nature of the injury. Implant 20 must traverse a distance which extends from healthy upper anterior vertebral body 58 through upper disc 42 which separates upper vertebral body 58 from upper anterior vertebral body 24. The implant 20 then traverses through upper hard bone area 40, across a void space 28 produced by the removal of a diseased or injured vertebral body 29, and across lower anterior vertebral body 26 to an opposite lower hard bone area 40 which is just above lower disc 42. The bottom portion of implant 20 can then extend across lower disc 42 to the next lower anterior vertebral body 60.

The implant 20 has annular bores 38 machined laterally through it near each of its ends. Preferably, the implant 20 will be curved to conform to the natural shape of the anterior spine 12 and will have open ends.

Figure 3:
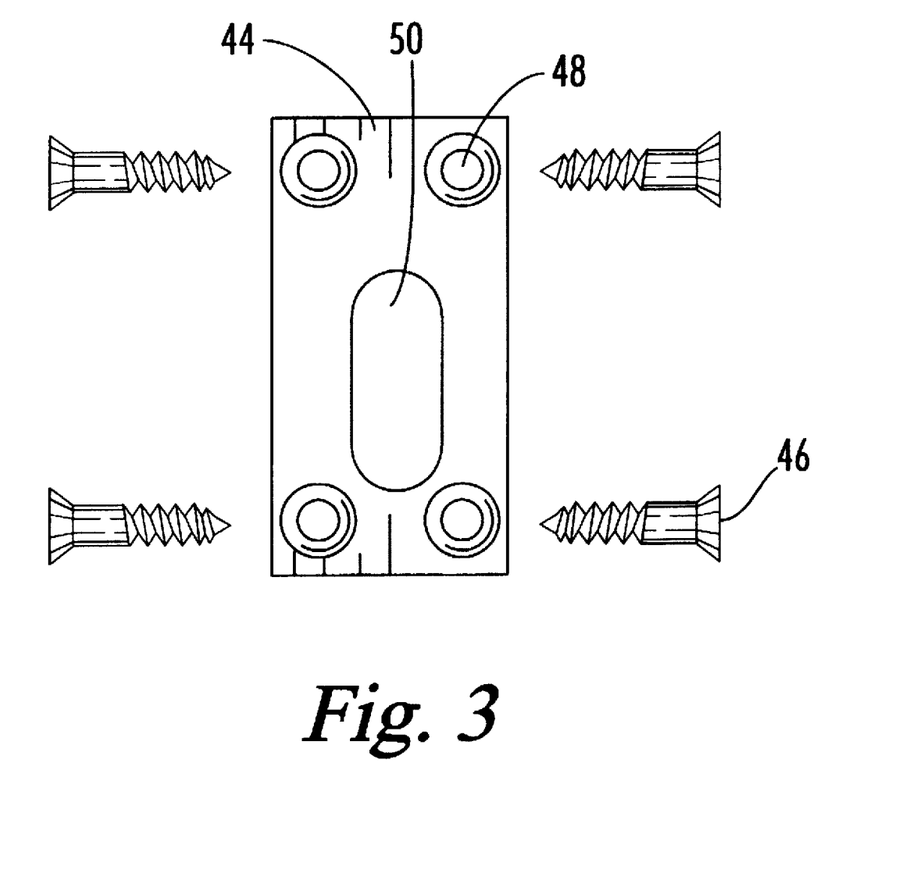
FIG. 3 is an exploded plan view of the retainer plate and retainer plate attachment screws used in a preferred embodiment of the invention.
Figure 9A:
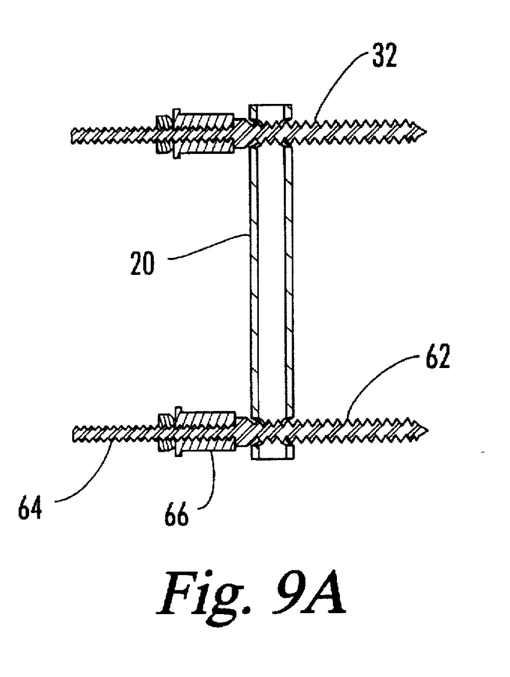
FIG. 9A is a cut-away side view of the implant and transverse locking bolts of the system.
Figure 9B:
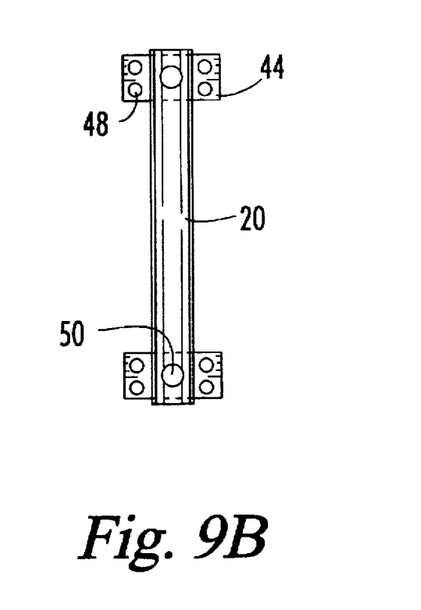
FIG. 9B is a side view of the implant and retainer plates of the system showing their respective orientations.

As best seen in FIGS. 1 and 9A, the transverse locking bolts 32 have a screw section 62 with self-tapping threads, a threaded bolt section 64 and a centrally disposed head 66. As best seen on FIGS. 3 and 9B, each retainer plate 44 has a transverse locking bolt port 50 and attachment screw ports 48. Retainer plate attachment screws 46 fit through attachment screw ports 48 and are used to mount retainer plate 44. Retainer plates 44 are preferably made of a biocompatible metal, such as stainless steel, and are preferably 3 mm thick.

Figure 2:
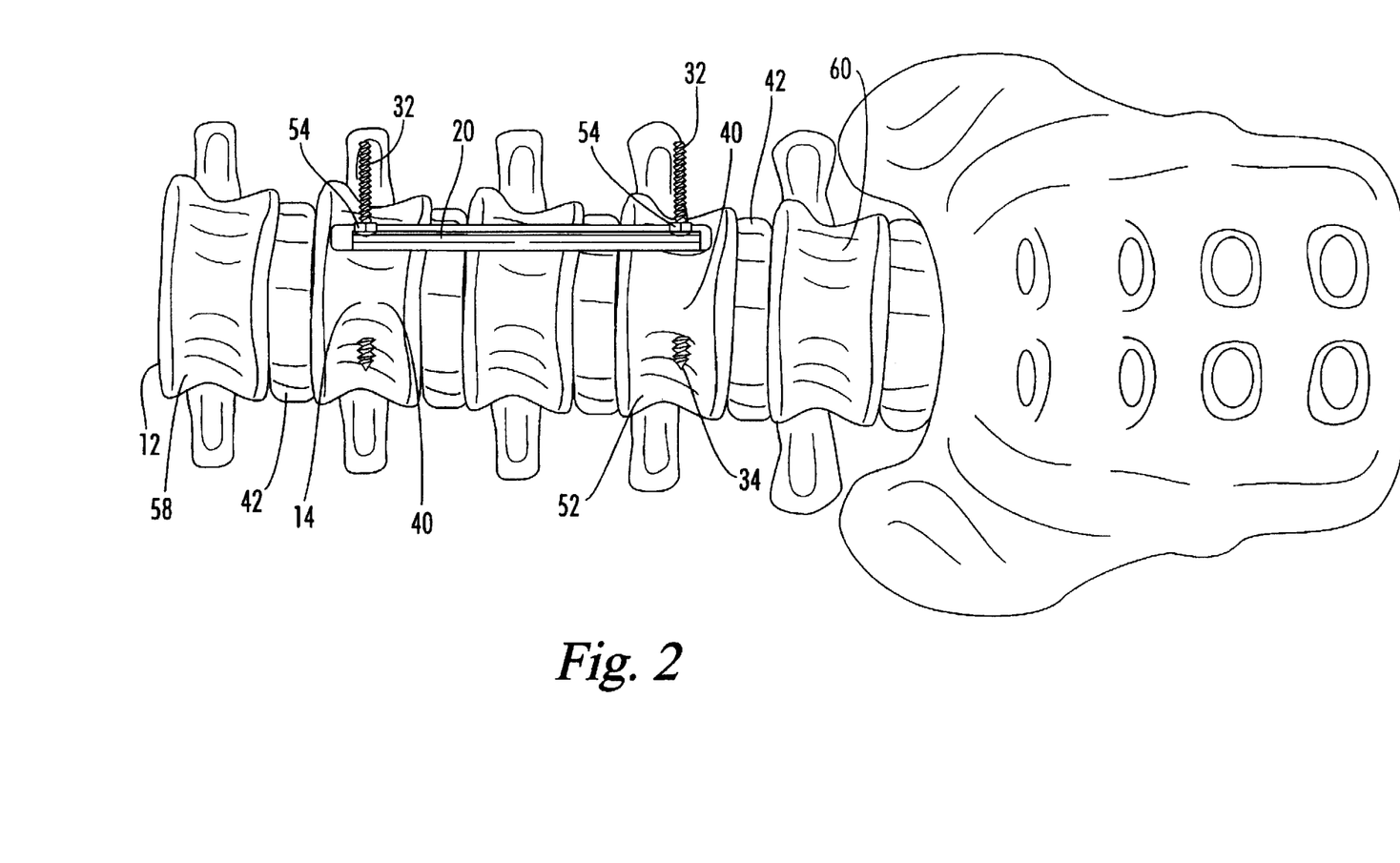
FIG. 2 is an anterior view of the lumbar region of a porcine spine as in FIG. 1, showing placement of the implant and lateral transverse positioning of the locking bolts as described in the preferred embodiment of the invention.
Figure 6:
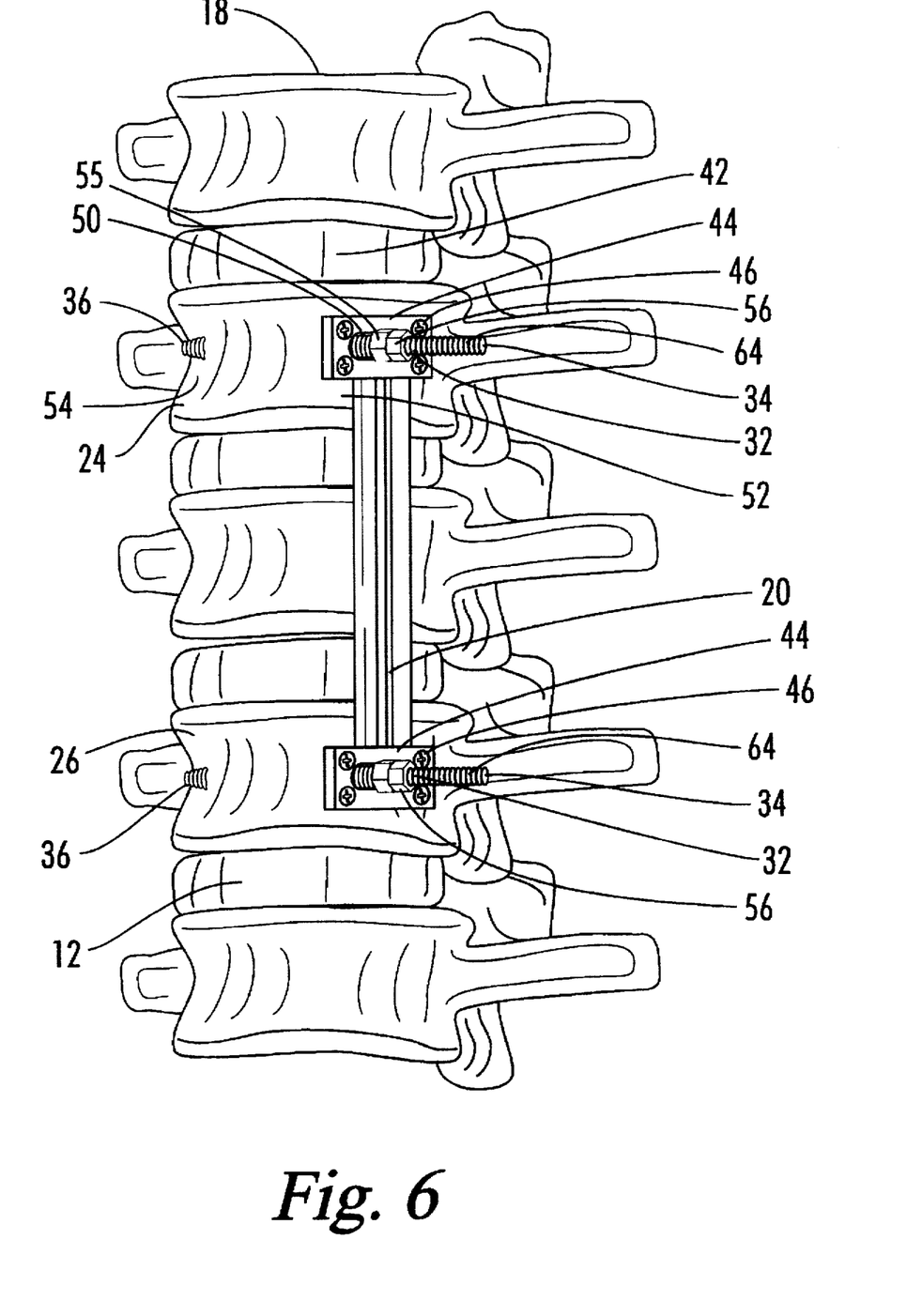
FIG. 6 is a lateral view of the anterior porcine spine, with the anterior spine in the normal vertical position. The transverse locking bolts, retainer plates, and implant cylinder of the invention are presented as installed.
Figure 7:
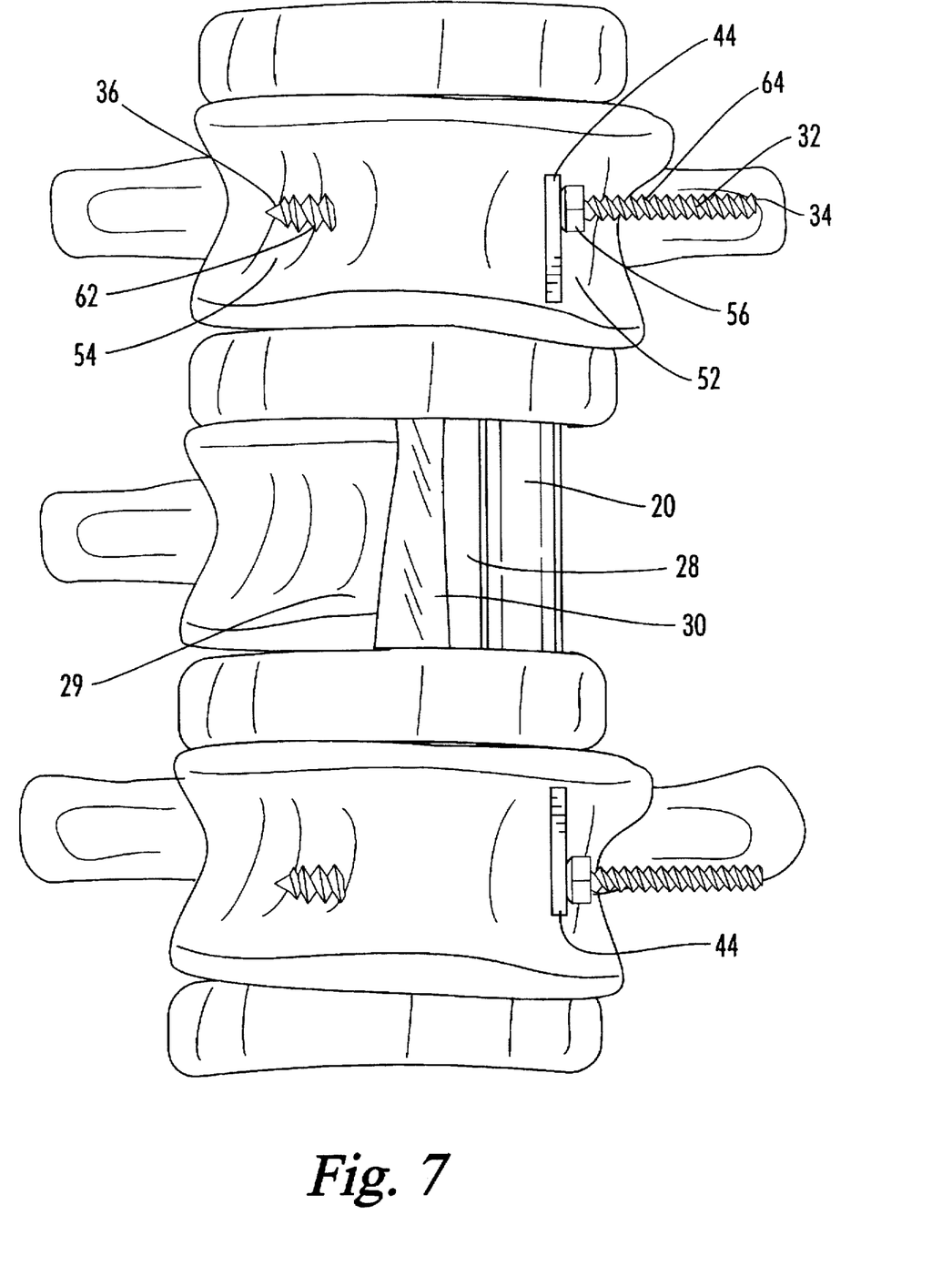
FIG. 7 is an enlarged distal lateral view of the anterior porcine spine in a vertical position, further illustrating the void resulting from removal of a diseased or injured vertebral body and the positioning of the implant across the void.

As seen in FIGS. 2, 6 and 7, the transverse locking bolts 32 are attached by inserting screw section 62 of bolt 32 through the proximal lateral surface 52 of the upper and lower adjacent anterior vertebral bodies 24, 26, through the hard bone area 40 between the proximal lateral surface 52 and the implant 20, through the bores 38 in the implant 20, through the hard bone area 40 between the implant 20 and the distal lateral surface 54 of the upper and lower adjacent anterior vertebral bodies 24, 26 and through the distal lateral surface 54 of the upper and lower adjacent anterior vertebral bodies 24, 26. The end 36 of screw section 62 extends laterally away from distal lateral surface 54 for a small distance. After inserting the screw section 62, the central head 66 lies on the proximal lateral surface 52 of the upper and lower adjacent anterior vertebral bodies 24, 26.

As best seen in FIG. 6, the bolt section 64 extends laterally away from the proximal lateral surface 52. The transverse locking bolts 32 are used to secure implant 20 and to provide medial-lateral and rotational support for the system 10.

As best seen in FIG. 6, bolt section 64 of the transverse locking bolt 32 fits through transverse locking bolt port 50 in retainer plate 44. In the preferred embodiment, retainer plate 44 further secures transverse locking bolt 32. Small and large locking nuts 55, 56 secure transverse locking bolts 32 to retainer plate 44. Retainer plate attachment screws 46 secure retainer plate 44 to the proximal lateral surface 52 of the upper and lower adjacent vertebral bodies 24, 26. The excess length of bolt section 64 which extends laterally from the locked implant 20 is cut off, flush with the surface.

The method of fixing the spine using the system 10 is described as follows. As shown in FIG. 7, implant 20 is designed to vertically span a void space 28, which was created by the removal of a diseased or injured vertebral body 29. As best seen in FIGS. 1, 2, 6 and 7, implant 20 is inserted into an upper slot 22 surgically created in an upper adjacent vertebral body 24 and into a lower slot 23 in a lower adjacent vertebral body 26. The upper and lower slots 22, 23 run from the void space 28 to the hard bone area 40 that lies just below or just above the discs 42 that separate the upper and lower adjacent vertebral bodies 24, 26 from the next respective upper and lower vertebral bodies 58, 60. Insertion into the upper and lower slots 22, 23 establishes an intraosseous central-middle column position for implant 20. This intraosseous position is a key safety feature provided by the system 10.

Figure 4:
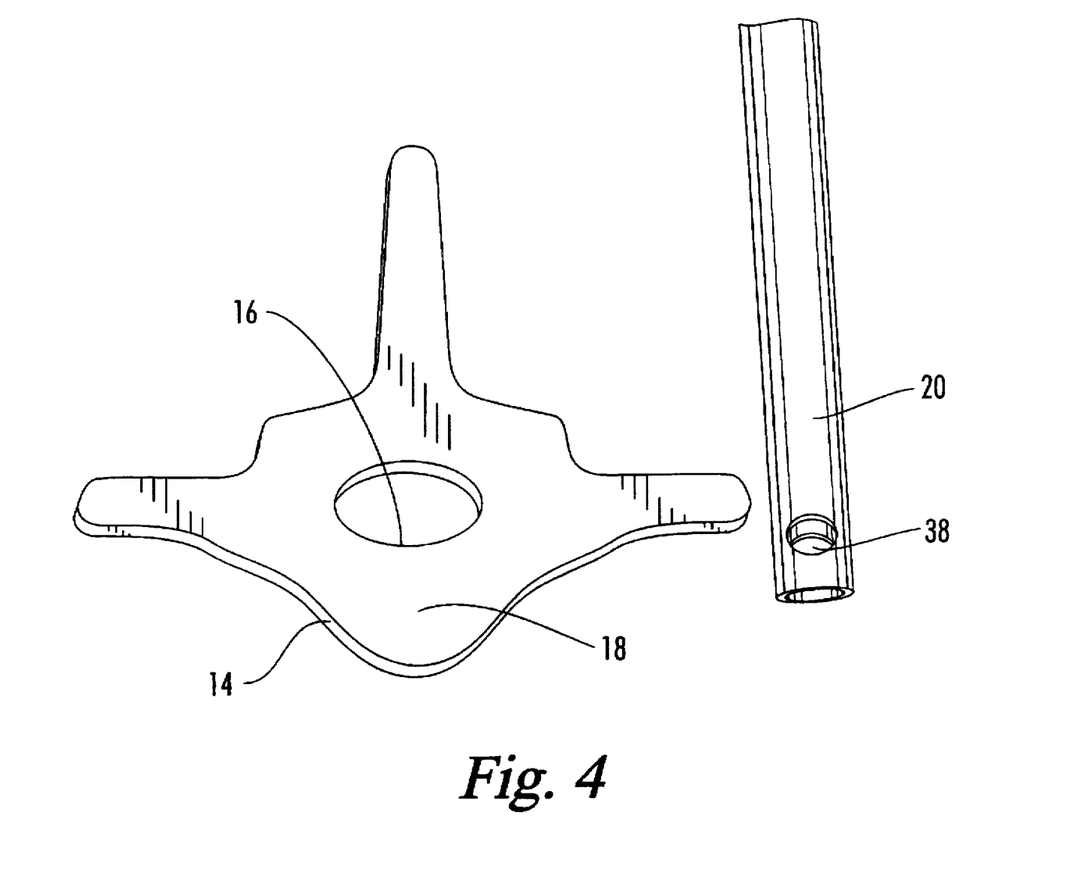
FIG. 4 is a perspective view looking from above a cross sectioned segment of the porcine spine with all of the surrounding tissues removed, showing the anterior surface, middle column area, and posterior surface of the anterior spine. It also shows the implant of the system of the invention prior to implantation.

As seen on FIGS. 1, 4, and 6, the upper and lower slots 22, 23 lie within the middle column area 18 of the anterior spine 12, that is, between the anterior surface 14 and the posterior surface 16 of the anterior spine 12. The insertion of implant 20 in the middle column area 18 of the anterior spine 12 provides biomechanical strength and reproduction of anatomic spinal sagittal curvature that other implants cannot duplicate.

As shown on FIGS. 2 and 6, once implant 20 is placed into upper and lower slots 22, 23, implant 20 is secured by transverse locking bolts 32 that run from a proximal lateral surface 52 of the anterior spine 12 through bores 38 in the implant 20, and finally through to the distal lateral surface 54 of the anterior spine 12. The transverse locking bolts 32 are inserted through the hard bone area 40 of the upper and lower adjacent vertebral bodies 24, 26. (FIGS. 1, 2 and 6) This hard bone area 40 is found just above or below the discs 42 that separate the upper and lower vertebral bodies 24, 26 from the next respective upper and lower anterior vertebral bodies 58, 60. (FIGS. 1 and 2) The addition of transverse locking bolts 32 strengthens the media-lateral and rotational support provided by the system 10.

Figure 5:
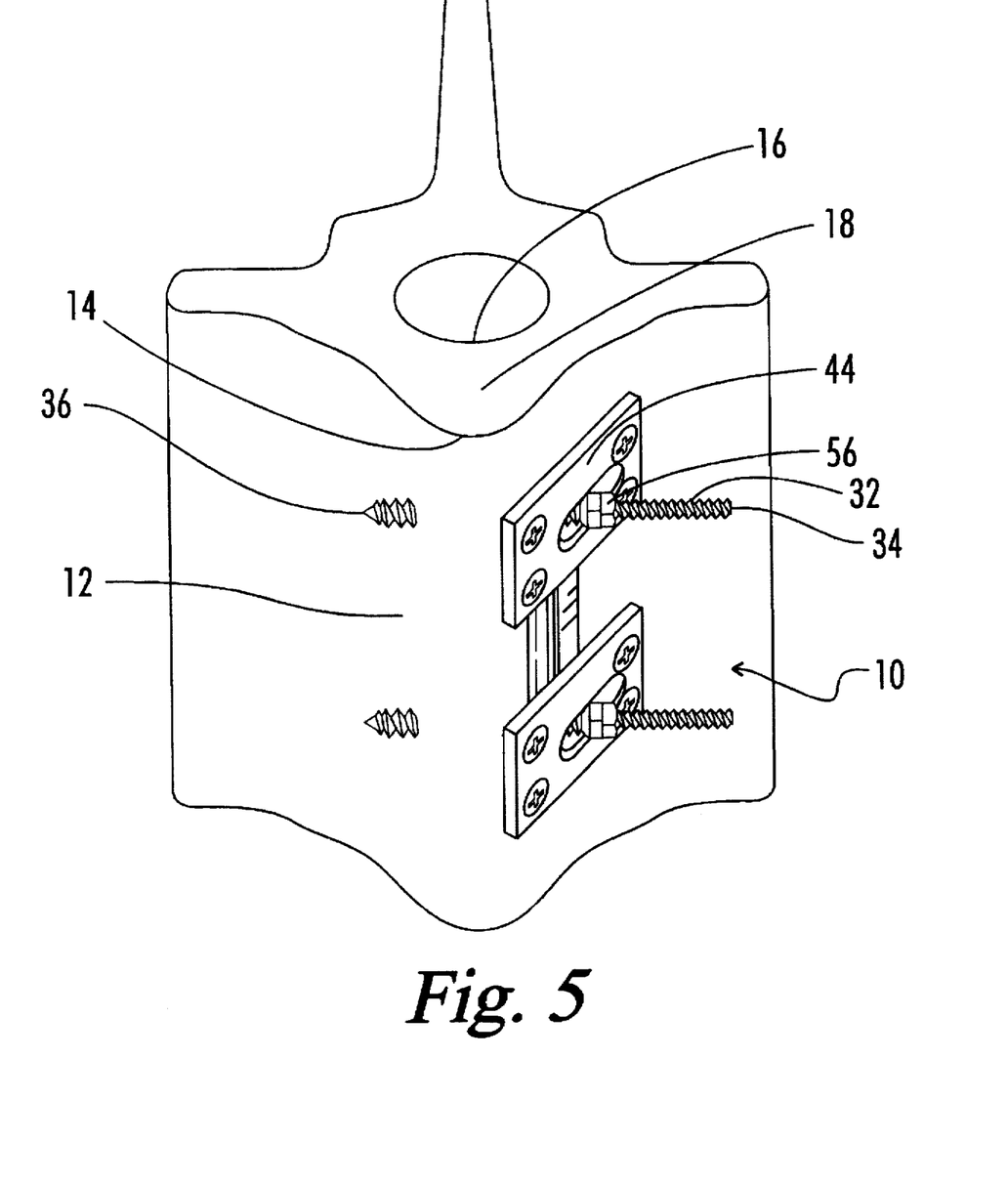
FIG. 5 is a perspective view of a cross-section of the anterior porcine spine as viewed from the top of the anterior spine. From this view, the transverse fixation locking bolts and the retainer plates can be seen.

As best seen in FIGS. 5, 6, and 7, each transverse locking bolt 32 is secured by the application of a retainer plate 44 followed by a first locking nut 55 and a second locking nut 56 to the proximal end 34 of the bolt section 64 of the transverse locking bolt 32 that extends laterally away from the proximal lateral surface 52 of the anterior spine 12. The transverse locking bolt 32 fits through a transverse locking bolt port 50 in the retainer plate 44. The retainer plate 44 is secured by retainer plate attachment screws 46 that are inserted through attachment screw ports 48 in the retainer plate 44 and into the proximal lateral surface 52 of the anterior spine 12. (FIGS. 3 and 6) The lateral positioning of transverse locking bolts 32 keeps it from damaging vital internal organs or structures that lie just anterior to the anterior spine 12.

After insertion of the implant 20, bone material is grafted over the implant 20 and grafted into void space 28. (See FIG. 7 for presentation of void space 28.) These grafts are used in an effort to achieve a union between bone and implant 20, which will increase the life of the implant 20.

The system 10 can utilize implants 20 of varying lengths, ranging typically from 7–13 cm. (FIG. 2) An implant 20 typically has a diameter of 8–12 mm, with walls approximately 1 mm thick. In a preferred embodiment of the system 10, a selection of the various components will be included in an intraoperative kit which will be taken into the operating room by the surgeon. In this embodiment, an inventory of implants 20 will be maintained by the hospital such that the surgeon can select one adequate to replace anywhere from one to four vertebral bodies, with variation in both implant diameter and curvature. Thus, the inventory will have multiple implants ranging from five to twenty-five centimeters in length, in increments of two centimeters. At each length preferably there will be implants 20 having two different diameters, ranging from ten to thirteen millimeters, with the smaller diameters for the cervical-thoracic spine areas and the larger diameters for the thoracic-lumbar spine. Also at each length and diameter for implants 20, there will be specific implants having a radius of curvature that varies from zero to ninety inches arc.

Prior to surgery, the surgeon will use x-ray and other techniques to estimate the appropriate length, diameter, and curvature for implant 20 that will be used. The surgeon will then select from the hospital's inventory anywhere from three to six implants 20 having dimensions which are close to the estimated needed length, diameter, and curvature. These will be placed into the intraoperative kit along with a plurality of transverse locking bolts 32, preferably ranging from approximately twenty millimeters to one hundred sixty millimeters, at six different incremental lengths in that range. Also in the intraoperative kit will be small, medium, and large retainer plates, with the median being approximately 30 millimeters by 15 millimeters by 3 millimeters thick, the small being five millimeters shorter at each length and width dimension, and the large being five millimeters longer at each respective dimension. The kit will further include four retainer plate attachment screws 46 along with small and large locking nuts 55 and 56.

The variety of lengths available for the implant 20 improves the effectiveness of the system 10. First of all, it allows a physician to immobilize the smallest portion of the spine possible, which results in improved function and longer lasting fusion of the injured spinal area. Furthermore, the varying lengths add modularity to the system 10. Modularity makes the system 10 user friendly in that it allows the system 10 to provide intraoperative exchangeable parts to better fit the patient.

The following experiments were performed to demonstrate the stability of the spinal fusion system of this invention. The biomechanical characteristics of the spinal fusion system were tested and compared to the intact spine as well as other constructs commonly used for anterior and posterior spinal instrumentation in a corpectomy model. There has not yet been a satisfactory anterior spinal implant.

Specimen preparation: Six porcine spines were harvested and used for biomechanical testing of the spinal fusion system. Six additional porcine spines were previously tested for biomechanical analysis of other commonly used anterior/posterior spinal constructs. All spines were harvested from adult pigs weighing approximately 400 pounds (1800N). The spines were disarticulated between T-12 and L-1 as well as L-6 and S-1. All spines were kept frozen. Testing was performed at room temperature after thawing. Muscle tissue was removed from the spines but all inter-vertebral ligaments and facet capsules were preserved.

Testing: All biomechanical testing was performed with a biaxial hydraulic testing machine (MTS, Minneapolis, Minn.). The implants were pre-conditioned with an axial load of 25% of the swine's body weight at 1 Hz for each spine. Axial and torsional test sequences were each separately performed four times, once for the intact spine (I) and three times with an implant.

The spines were instrumented between L-2 and L-4. A complete corpectomy of L-3 including the posterior longitudinal ligaments was performed to simulate an unstable burst fracture or corpectomy for vertebral body tumor. The two spinal fusion systems tested were the spinal fusion system alone (S) and the spinal fusion system plus an anterior strut graft (SA). Three other commonly available constructs were tested under identical conditions for comparison. These were performed on the second set of six spines. These included the posterior Steffee plate/pedicle screws (P), posterior Steffee plate/pedicle screws plus anterior strut graft (PA), and the anterior Kaneda device plus anterior strut graft (AA). The anterior Kaneda device without strut graft failed easily and was not included in biomechanical testing. Axial compression was performed using three different loads, 100% body weight (BW), 150% BW, and 200% BW. Torsion was tested at 2°, 4° and 6°. Load deformation curves and torque angle curves were calculated for each specimen.

Implants: The implant 20 of the spinal fusion system was a closed cylinder, 13 mm in diameter. Seven millimeter locking bolts 32 were applied through the L-2 and L-4 vertebral bodies. The Steffee plate/pedical screws were 7 mm×40 mm and placed bilaterally into the L-2 and L-4 vertebral bodies through the pedicles. The Kaneda tetra spike plates were impacted into place on the right anterior lateral aspect of the L-2 and L-4 vertebral bodies and 40–50 mm screws inserted through the plates obtaining purchase on the contralateral cortex. The anterior strut graft was a wood block that was wedged into the carpectomy site.

Figure 8:
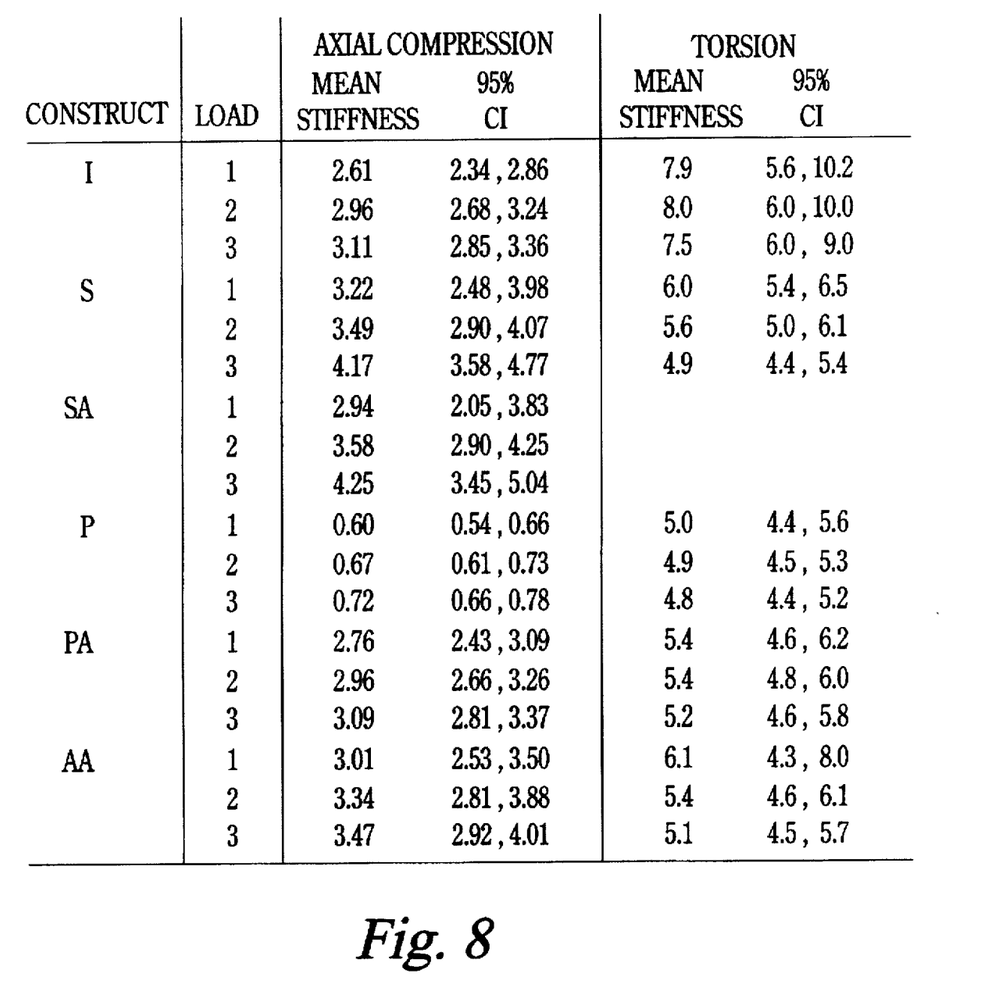
FIG. 8 is a table reporting the results of stress experiments performed to compare the spinal fusion system of the present invention with prior art devices.

Results: The results of the experiments are described in Table 1 of FIG. 8. Briefly, the spinal fusion system 10 of the present invention was superior to the posterior Steffee plate/pedicle construct in axial compression. There was no statistical difference between the spinal fusion system and the Kaneda device with the anterior strut graft. However, all the Kaneda devices failed under axial compression without a strut graft. There was no statistical difference in axial stiffness in the spinal fusion system with or without strut grafting. Although the Spinal Fusion System had less torsional rigidity than the intact spine, there was no statistical difference noted between the spinal fusion system and the other constructs tested. Therefore, the spinal fusion system is at least as effective, and in some cases, more effective than currently used anterior and posterior constructs in providing stability to a short segment anterior fusion of the spine.

Thus, although there have been described particular embodiments of the present invention of a new and useful Low Profile Intraosseous Anterior Spinal Fusion System and Method, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What we claim is:

1. A spinal implant for use in short segment anterior fusion of a patient's spine after removal of a diseased or injured anterior vertebral body, the removal of the diseased or injured anterior vertebral body creating a void space in the patient's spine, said implant comprising:
   a. spinal support means for fusing the patient's anterior spine and for providing load sharing support of the patient's spine when said support means is located in an anterior intraosseous position within the patient's spine, said support means comprising a cylinder of a length sufficient to traverse a distance extending from a hard bone area in an upper anterior vertebral body of the patient's spine above the void space, across the void space, and to an opposite hard bone area in a lower anterior vertebral body of the patient's spine below the void space, said cylinder having transverse bores near each end; and
   b. transverse fixation means for securing said spinal support means within the patient's spine, said fixation means adapted for attachment by inserting said fixation means through a first lateral surface of the upper and lower anterior vertebral bodies above and below the void space, through the hard bone area between the first lateral surface of the upper and lower vertebral bodies and said spinal support means, through said bores in said cylinder means, through the hard bone area between said spinal support means and a second lateral surface of the upper and lower anterior vertebral bodies, and through the second lateral surface of said upper and said lower anterior vertebral bodies.

2. The implant described in claim 1 wherein the spinal support means provides primary load sharing support as compared to any load shared by said transverse fixation means.

3. The implant described in claim 1 wherein said transverse fixation means comprises a locking bolt.

4. The implant described in claim 1 wherein said cylinder is curved to conform to a natural curvature of the patient's spine.

5. A spinal implant for use in short segment anterior fusion of a patient's spine after removal of a diseased or injured anterior vertebral body, the removal of the diseased or injured anterior vertebral body creating a void space in the patient's spine, said implant comprising:
   a. spinal support means for fusing the patient's anterior spine and for providing load sharing support of the patient's spine when said support means is located in an anterior intraosseous position within the patient's spine, said support means comprising a cylinder of a length sufficient to traverse a distance extending from a hard bone area in an upper anterior vertebral body of the patient's spine above the void space, across the void space, and to an opposite hard bone area in a lower anterior vertebral body of the patient's spine below the void space, said cylinder having transverse bores near each end; and
   b. transverse securing means for securing said spinal support means within the patient's spine by passing said transverse securing means through said bores in said spinal support means; and
   c. a retaining plate mountable to a lateral end of said transverse securing means, said retaining plate including a bore for receiving said transverse securing means and at least one mounting port adjacent to said bore.

6. The implant described in claim 5 wherein at least one nut is attached to said lateral end of said transverse securing means proximate to said retainer plate.

7. A spinal implant for use in short segment anterior fusion of a patient's spine after removal of a diseased or injured anterior vertebral body, the removal of the diseased or injured anterior vertebral body creating a void space in the patient's spine, said implant comprising:
   a. spinal support means for fusing the patient's anterior spine and for providing load sharing support of the patient's spine when said support means is located in an anterior intraosseous position within the patient's spine, said support means comprising a cylinder of a length sufficient to traverse a distance extending from a hard bone area in an upper anterior vertebral body of the patient's spine above the void space, across the void space, and to an opposite hard bone area in a lower anterior vertebral body of the patient's spine below the void space, said cylinder having transverse bores near each end;
   b. transverse fixation means for securing said spinal support means within the patient's spine, said fixation means adapted for attachment by inserting said fixation means through a first lateral surface of the upper and lower anterior vertebral bodies above and below the void space, through the hard bone area between the first lateral surface of the upper and lower vertebral bodies and said spinal support means, through said bores in said cylinder means, through the hard bone area between said spinal support means and a second lateral surface of the upper and lower anterior vertebral bodies, and through the second lateral surface of said upper and said lower anterior vertebral bodies; and c. a retaining plate attached to a lateral end of said transverse fixation means, said lateral end of said transverse fixation means protruding from the first lateral surface of the upper and lower anterior vertebral bodies, the retainer plate including a plurality of mounting ports and a central bore through which said lateral end of said transverse fixation means protrudes, said mounting ports located on opposite sides of said central bore.

8. The implant described in claim 2 wherein said transverse fixation means comprises a locking bolt.

9. The implant described in claim 7 wherein at least one nut is attached to said lateral end of said transverse fixation means proximate to said retainer plate.

10. The implant described in claim 7 wherein said cylinder is curved to conform to a natural curvature of the patient's spine.

11. A spinal implant for use in short segment anterior fusion of a patient's spine after removal of a diseased or injured anterior vertebral body, the removal of the diseased or injured anterior vertebral body creating a void space in the patient's spine, said implant comprising:

a. a cylinder of a length sufficient to traverse a distance extending from a hard bone area in an upper anterior vertebral body of the patient's spine above the void space, across the void space, and to an opposite hard bone area in a lower anterior vertebral body of the patient's spine below the void space, said cylinder having transverse bores near each end;

b. transverse fixation means for securing said cylinder within the patient's spine, said fixation means adapted for attachment by inserting said fixation means through a first lateral surface of the upper and lower anterior vertebral bodies above and below the void space, through the hard bone area between the first lateral surface of the upper and lower vertebral bodies and said cylinder, through said bores in said cylinder, through the hard bone area between said cylinder and a second lateral surface of the upper and lower anterior vertebral bodies, and through the second lateral surface of said upper and said lower anterior vertebral bodies; and c. a retaining plate attached to a lateral end of said transverse fixation means, said lateral end of said transverse fixation means protruding from the first lateral surface of the upper and lower anterior vertebral bodies, the retainer plate including a plurality of mounting ports and a central bore through which said lateral end of said transverse fixation means protrudes, said mounting ports located on opposite sides of said central bore.

12. The implant described in claim 11 wherein said transverse fixation means comprises a locking bolt.

13. The implant described in claim 11 wherein at least one nut is attached to said lateral end of said transverse fixation means proximate to said retainer plate.

14. The implant described in claim 11 wherein said cylinder is curved to conform to a natural curvature of the patient's spine.

15. A spinal implant for use in short segment anterior fusion of a patient's spine after removal of a diseased or injured anterior vertebral body, the removal of the diseased or injured anterior vertebral body creating a void space in the patient's spine, said implant comprising:

a. spinal support means for rising the patient's anterior spine and for providing load sharing support of the patient's spine when said support means is located in an anterior intraosseous position within the patient's spine, said support means comprising a cylinder of a length sufficient to traverse a distance extending from a hard bone area in an upper anterior vertebral body of the patient's spine above the void space, across the void space, and to an opposite hard bone area in a lower anterior vertebral body of the patient's spine below the void space, said cylinder having transverse bores near each end; and b. transverse securing means for securing said spinal support means within the patient's spine, said transverse securing means passing through said bores in said cylinder means, said bores positioned so that said transverse securing means is located at a fixed vertical position when transversely mounted, said bores having a diameter substantially similar to an outer diameter of the transverse securing means so as to maintain the transverse securing means at the fixed vertical position along the spinal support means.

* * * * *